United States Patent [19]
Stelzer et al.

[11] Patent Number: 5,814,669
[45] Date of Patent: Sep. 29, 1998

[54] AMINO ACID DERIVATIVES AND THEIR USE AS PESTICIDES

[75] Inventors: Uwe Stelzer, Burscheid; Carl Casser, Köln; Thomas Seitz, Langenfeld, all of Germany

[73] Assignee: Bayer Aktiengesellschaft, Leverkusen, Germany

[21] Appl. No.: 765,470

[22] PCT Filed: Jun. 16, 1995

[86] PCT No.: PCT/EP95/02321

§ 371 Date: Dec. 20, 1996

§ 102(e) Date: Dec. 20, 1996

[87] PCT Pub. No.: WO96/00718

PCT Pub. Date: Jan. 1, 1996

[30] Foreign Application Priority Data

Jun. 28, 1994 [DE] Germany .......... 44 22 567.9
Jan. 17, 1995 [DE] Germany .......... 195 01 175.9

[51] Int. Cl.⁶ .......... A61K 31/165; C07C 233/05; C07C 231/10

[52] U.S. Cl. .......... 514/626; 514/456; 549/407; 564/194; 564/196

[58] Field of Search .......... 564/194, 196; 514/626, 456; 549/407

[56] References Cited

U.S. PATENT DOCUMENTS 4,918,105  4/1990  Cartwiright et al. .......... 514/575

FOREIGN PATENT DOCUMENTS 0274453  7/1988  European Pat. Off. .
0398072  11/1990  European Pat. Off. .
0587110  3/1994  European Pat. Off. .

*Primary Examiner*—Shailendra Kumar
*Attorney, Agent, or Firm*—Sprung Kramer Schaefer & Briscoe

[57] ABSTRACT

The invention relates to novel amino acid derivatives, to a process for their preparation and to their use as pesticides, in particular as fungicides, and as intermediates for preparing known substituted amino acid derivatives with fungicidal activity.

5 Claims, No Drawings

AMINO ACID DERIVATIVES AND THEIR USE AS PESTICIDES

The invention relates novel amino acid derivatives, to a process for their preparation and to their use as pesticides, in particular as fungicides, and as intermediates for preparing known substituted amino acid derivatives with fungicidal activity.

It is already known that certain substituted amino acid derivatives have fungicidal properties and are obtained by reacting substituted amino acids with appropriate amines (compare EP-A 0 472 995).

Furthermore, certain amines of substituted amino acids are known (compare EP-A 0 587 110).

Novel compounds of the general formula (I)

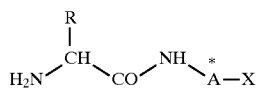

in which

A represents straight-chain or branched alkylene

X represents unsubstituted or substituted aryl or represents unsubstituted or substituted heterocyclyl, and R represents straight-chain, branched or cyclic alkyl, and their salts have now been found, excepting the compounds $N^1$-[1-(5-cyano-2-benzofuranyl)ethyl]-L-valinamide, $N^1$-[1-(5-chloro-2-benzofuranyl)ethyl]-L-valinamide, $N^1$-[1-(5-fluoro-2-benzofuranyl)ethyl]-L-valinamide, $N^1$-[1-(3-methyl-2-benzothiophenyl)ethyl-L-valinamide.

Aryl preferably represents hereinafter in each case unsubstituted or substituted phenyl, benzothiophene, benzofuran, suitable and preferred substituents being halogen, cyano, alkyl, halogenoalkyl, alkoxy and halogenoalkoxy.

Alkyl preferably represents hereinafter straight-chain or branched alkyl with 1 to 6, in particular 1 to 4 carbon atoms such as methyl, ethyl, n-propyl, n-, i-, t-butyl and, in particular, i-propyl and s-butyl and represents cyclic alkyl with 3 to 6 carbon atoms such as, in particular, cyclopentyl.

Alkylene preferably represents hereinafter straight-chain or branched alkylene with 1 to 6, preferably 1–4 carbon atoms such as, in particular 1,1-ethylene, 1,2-ethylene, 1,1-propylene, 1-methyl-1,2-ethylene, 2-methyl-1,2-ethylene, 1,1-dimethyl-methylene.

Preferred compounds are those of the formula (I)

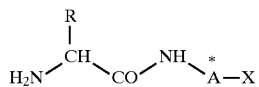

in which

A represents 1,1-ethylene or 1,2-ethylene,

X represents in each case unsubstituted or substituted phenyl, benzothiophene or benzofuran, substituents which are mentioned being halogen, cyano, alkyl, halogenoalkyl, alkoxy and halogenoalkoxy, and R represents i-propyl, s-butyl or cyclopentyl, and their salts, excepting the compounds $N^1$-[1-(5-cyano-2-benzofuranyl)ethyl]-L-valinamide, $N^1$-[1-(5-chloro-2-benzofuranyl)ethyl]-L-valinamide, $N^1$-[1-(5-fluoro-2-benzofuranyl)ethyl]-L-valinamide, $N^1$-[1-(3-methyl-2-benzothiophenyl)ethyl-L-valinamide.

Particularly preferred compounds are those of the formula (I) in which

R represents 1,1-ethylene or 1,2-ethylene,

X represents phenyl, 2-benzothiophen or 2-benzofuran, which are optionally substituted in the phenyl ring once to three times by methyl, methoxy, trifluoromethyl, trifluoromethoxy, ethyl, ethoxy, fluorine, chlorine and/or cyano, and R represents i-propyl or s-butyl, and their salts, excepting the abovementioned compounds.

Very particularly preferred compounds are those of the formula (Ia)

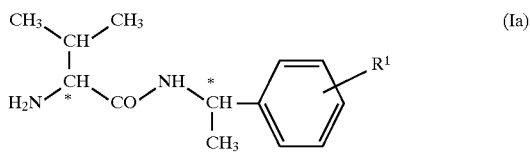

in which $R^1$ represents chlorine, methyl, ethyl or methoxy, and their salts.

The compounds of the formula (I) contain two centres of chirality and may thus exist in various enantiomeric and diastereomeric mixtures which can, where appropriate, be separated in a conventional way. Both the pure enantiomers and diastereomers and the mixtures are claimed according to the invention.

For the sake of simplicity reference will always be made hereinafter to compounds of the formula (I) although both the pure compounds and the mixtures with various contents of isomeric, enantiomeric and diastereomeric compounds are meant.

A corresponding statement applies to the compounds of the formulae (III) and (IV) which also follow.

It has furthermore been found that the compounds of the formula (I)

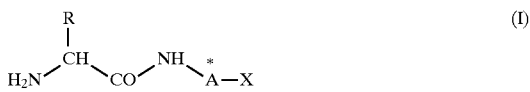

in which

A represents straight-chain or branched alkylene

X represents unsubstituted or substituted aryl or represents unsubstituted or substituted heterocyclyl, and R represents straight-chain, branched or cyclic alkyl, and their salts, are obtained in surprisingly good yield when oxazolidinediones of the formula (II)

in which

R has the abovementioned meaning, are reacted with amines of the general formula (III)

in which

A and X have the abovementioned meanings, in the presence of a diluent and, where appropriate, in the presence of a reaction aid.

It has additionally been found that the novel amino acid derivatives of the formula (I) can be used as pesticides.

Preferred compounds of the formula (I) are those in which the underlying amino acid is the compound with the L configuration, and the amine of the formula (III) which is employed is either racemic or has the R configuration or the S configuration at the asymmetric carbon atom.

The oxazolidinediones of the formula (II) to be used as starting material for carrying out the process according to the invention are known (compare Angew. Chem. 93, 793 (1981)) and can be obtained by the process described therein, by reacting the appropriate amino acids with phosgene in a conventional way.

The amines which are additionally to be used as starting materials for carrying out the process according to the invention are generally defined by formula (III).

The amines of the formula (III) are generally known compounds of organic chemistry.

Diluents suitable for the process according to the invention are inert organic solvents such as: ketones such as acetone or ethyl methyl ketone; esters such as ethyl or methyl acetate; amides such as dimethylformamide; nitriles such as acetonitrile; chlorohydrocarbons such as methylene chloride or tetrachloromethane; hydrocarbons such as toluene or ethers such as tetrahydrofuran and, where appropriate, water and mixtures thereof.

The process according to the invention is carried out, where appropriate, in the presence of a buffer as reaction aid. In this connection it is possible to employ all conventional buffer systems such as, in particular, sodium boranate/boric acid.

The temperatures when carrying out the process according to the invention can be varied within a relatively wide range. The temperatures are generally from −100° to +150° C., preferably from −60° to +100° C.

When carrying out the process according to the invention, in general 1 to 10 mol, preferably 1 to 5 mol of amine of the formula (III) are employed per mole of oxazolidinone of the formula (II).

In a particular form for carrying out the process according to the invention, the amine of the formula (III) is simultaneously also employed as diluent.

The working up and isolation of the compounds takes place by generally customary and known methods.

The invention embraces both the pure isomers and the mixtures of the compounds of the formula (I). These mixtures can be fractionated into the components by conventional methods, for example selective crystallization from suitable solvents or chromatography on silica gel or aluminium oxide. Racemates can be fractionated into the individual enantiomers by customary methods, for example by salt formation with optically active acids such as camphorsulphonic acid or dibenzoyltartaric acid and selective crystallization or by derivatization with suitable optically active reagents, separation of the diastereomeric derivatives and cleavage back or separation on optically active column material.

The compounds of the formula (I) according to the invention have a strong microbicidal action and can be employed in practice for controlling unwanted microorganisms. The active substances are suitable for use as crop protection agents, in particular as fungicides.

At appropriate application rates, the compounds according to the invention also show a herbicidal or insecticidal action.

Some causes of fungal diseases which are covered by the general terms listed above may be mentioned by way of example but without limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubense;*
Plasmopara species, such as, for example, *Plasmopara viticola;*
Peronospora species, such as, for example, *Peronospora pisi* or *Peronospora brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturai species, such as, for example, *Venturia inaequalis;*
Pyrenophora species, such as, for example, *Pyrenophora teres* or *Pyrenophora graminea* (conidiaform: Drechslera, synonym: Helminthosporium);
Cochliobolus species, such as, for example, *Cochliobolus sativus* (conidiaform: Drechslera, synonym: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Altemaria species, such as, for example, *Altemaria brassicae;*
Pseudocercosporella species, such as, for example, *Pseudocercosporella herpotrichoides.*

Very good tolerability of the active substances by plants at the concentrations necessary to control plant diseases allows treatment of the above-ground parts of plants, of plant and seed materials and of the soil.

The active substances can be converted into customary formulations depending on their respective physical and/or chemical properties, such as solutions, emulsions, suspensions, powders, foams, pastes, granules, aerosols, microencapsulations in polymeric materials and in coating compositions for seeds, and ULV cooled and warm fogging formulations.

These formulations are produced in a known manner, for example by mixing the active substances with extenders, that is to say liquid solvents, liquefied gases which are under pressure and/or solid carriers, where appropriate using surface-active agents, that is to say emulsifiers and/or dispersants and/or foam-generating agents. In the event that water is used as extender it is possible, for example, also to use organic solvents as auxiliary solvents. Suitable liquid solvents are essentially: aromatic compounds such as xylene, toluene, alkylnaphthalenes, chlorinated aromatic compounds or chlorinated aliphatic hydrocarbons, such as chlorobenzenes, chloroethylenes, or methylene chloride, aliphatic hydrocarbons such as cyclohexane or paraffins, for example petroleum fractions, alcohols such as butanol or glycol, and their ethers and esters, ketones such as acetone, methyl ethyl ketone, methyl isobutyl ketone or cyclohexanone, highly polar solvents such as dimethyl formamide or dimethyl sulphoxide, and water; liquefied gaseous extenders or carriers meaning liquids which are gaseous at normal temperature and under atmospheric pressure, for example aerosol propellant gases such as halogenated hydrocarbons, and butane, propane, nitrogen and carbon dioxide; suitable solid carriers are: for example natural rock powders such as kaolins, aluminas, talc, chalk, quartz, attapulgite, montmorillonite or diatomaceous earth and synthetic rock powders such as highly disperse silica, aluminium oxide and silicates; suitable solid carriers for granules are: for example crushed and fractionated natural rocks such as calcite, marble, pumice, sepiolite, dolomite and synthetic granules of inorganic and organic powders, and granules from organic materials such as sawdust, coconut shells, corn stalks and tobacco stalks; suitable emulsifiers and/or foam-generating agents are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin sulphite waste liquors and methylcellulose.

It is possible to use in the formulations adhesives such as carboxymethylcellulose, natural and synthetic, powdered, granular or latex-like polymers such as gum arabic, polyvinyl alcohol, polyvinyl acetate, and natural phospholipids such as cephalins and lecithins and synthetic phospholipids. Other possible additives are mineral and vegetable oils.

It is possible to use colouring agents such as inorganic pigments, for example iron oxide, titanium oxide, Prussian blue and organic colouring agents such as alizarin, azo and metal phthalocyanine dyes and trace nutrients such as salts of iron, manganese, boron, copper, cobalt, molybdenum and zinc.

The formulations generally contain between 0.1 and 95% by weight of active substance, preferably between 0.5 and 90%.

The active substances according to the invention can be used as such or in their formulations also mixed with known fungicides, bactericides, acaricides, nematicides or insecticides in order thus, for example, to widen the spectrum of action or prevent development of resistance.

Suitable for mixtures are, for example:

Fungicides:
2-Aminobutane; 2-anilino4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxy-phenyl)acetamide; 8-hydroxyquinoline sulphate; methyl (E)-2-{2-[6-(2-cyanophenoxy)-pyrimidin-4-yloxy]phenyl}-3-methoxyacrylate; methyl (E)-methoximino[alpha-(o-tolyloxy)-o-tolyl] acetate; 2-phenylphenol (OPP), aldimorph, ampropylfos, anilazin, azaconazole, benalaxyl, benodanil, benomyl, binapacryl, biphenyl, bitertanol, blasticidin-S, bromu-conazole, bupirimate, buthiobate, calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanide, diclomezine, dicloran, diethofencarb, difenoconazole, dimethirimol, dimethomorph, diniconazole, dinocap, diphenylamine, dipyrithione, ditalimfos, dithianone, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachloro benzene, hexaconazole, hymexazole, imazalil, imibenconazole, iminoctadine, iprobenfos (IBP), iprodione, isoprothiolane, kasugamycin, copper preparations such as: copper hydroxide, copper napthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxine, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:
Bronopol, dichlorophen, nitrapyrin, nickel dimethyldithiocarbamate, kasugamycin, octhilinone, furancarboxylic acid, oxytetracycline, probenazole, streptromycin, tecloftalam, copper sulphate and other copper preparations.

Insecticides / acaricides / nematicides:
Abamectin, abamectin, acephate, acrinathrin, alanycarb, aldicarb, alphamethrin, amitraz, avermectin, AZ 60541, azadirachtin, azinphos A, azinphos M, azocyclotin, *Bacillus thuringiensis,* 4-bromo-2-(4-chlorophenyl)-1-(ethoxymethyl)-5-(trifluoromethyl)-1H-pyrrole-3-carbonitrile, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, chloethocarb, chlorethoxyfos, chloretoxyfos, chlorfenvinphos, chlorfluazuron, chlormephos, N-[(6-chloro-3-pyridinyl)-methyl]-N'-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinone, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fiibfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, nitenpyram omethoate, oxamyl, oxydemethon M, oxydeprofos, parathion A, parathion M, permethrin, phenthoate, phorate, phosalone, phosmet, phosphamdon, phoxim, pirimicarb, pirimiphos M, primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos, salithion, sebufos, silafluofen, sulfotep, sulprofos, tebufenozide, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to have a mixture with other known active substances such as herbicides or with fertilizers and growth regulators.

The active substances can be used as such, in the form of their formulations or the use forms prepared therefrom, such as ready-to-use solutions, suspensions, wettable powders, pastes, soluble powders, dusting preparations and granules. They are used in the customary manner, for example by watering, spraying, atomizing, scattering, dusting, foaming, brushing on and the like. It is furthermore possible to apply the active substances by the ultra low volume method or to inject the active substance preparation or the active substance itself into the soil. The seeds of the plants can also be treated.

In the treatment of parts of plants, the active substance concentrations in the use forms can be varied in a relatively wide range: they are in general between 1 and 0.0001% by weight, preferably between 0.5 and 0.001% by weight.

The amounts of active substance generally required for treating seeds are from 0.001 to 50 g per kilogram of seeds, preferably 0.01 to 10 g.

The concentrations of active substance required for treating the soil are from 0.00001 to 0.1% by weight, preferably from 0.0001 to 0.02% by weight, at the site of action.

The compounds of the formula (I) and (Ia) according to the invention are also particularly suitable as intermediates for preparing known substituted amino acid derivatives with fungicidal activity, of the general formula (IV)

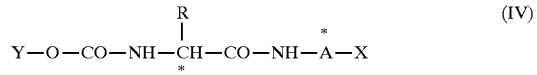

in which

R, A and X have the abovementioned meanings, and

Y represents aryl, aralkyl or alkyl, preferably i-propyl and s-butyl, or represents phenyl, benzyl or cyclopentyl, each of which is optionally substituted by chlorine, methyl and/or methoxy.

The amino acid derivatives of the formula (IV) are moreover obtained when the compounds of the formula (I) or (Ia)

a) are reacted with acid derivatives of the general formula (V)

Y—O—CO—Z        (V)

in which

Y has the abovementioned meaning, and

Z represents halogen or the group —O—CO—OY, in the presence of a diluent and, where appropriate, in the presence of an acid-binding agent and, where appropriate, in the presence of a catalyst at temperatures between −100° and +120° C.; or b) are reacted first with phosgene in the presence of a diluent and, where appropriate, in the presence of an acid-binding agent at temperatures between −100° and +120° C., and subsequently, without isolating the isocyanates or carbamoyl chlorides formed as intermediates, with alcohols of the general formula (VI)

Y—OH        (VI)

in which

Y has the abovementioned meaning, at temperatures between −100° and +120° C.

Process variants (a) and (b) moreover provide the compounds of the formula (IV) in virtually quantitative yield.

A particular advantage furthermore lies in the totality of the processes, that is to say in the direct combination of the process according to the invention for preparing the compounds of the formula (I) or (Ia) and further reaction thereof according to process variants (a) and (b).

It is also possible moreover to react the compounds of the formula (I) or (Ia) further directly without intermediate isolation.

The acid derivatives to be used as starting materials for carrying out process variant (a) according to the invention are generally defined by formula (V). In this formula, Y has the abovementioned meanings. Z preferably represents chlorine, bromine or the group —O—CO—OY.

The acid derivatives of the formula (V) are generally known compounds of organic chemistry.

The alcohols to be used as starting materials for carrying out process variant (b) according to the invention are generally defined by formula (VI). In this formula, Y has the abovementioned meanings.

The alcohols of the formula (VI) are generally known compounds of organic chemistry.

Diluents suitable for process variants (a) and (b) according to the invention are inert organic solvents such as: ketones, such as acetone or ethyl methyl ketone; esters such as ethyl or methyl acetate; amides such as dimethylformamide; nitriles such as acetonitrile; chlorohydrocarbons such as methylene chloride or tetrachloromethane; hydrocarbons such as toluene or ethers such as tetrahydrofuran and, where appropriate, water and mixtures thereof.

Suitable acid-binding agents for process variants (a) and (b) according to the invention are customary inorganic and organic acid binders. These preferably include tertiary amines such as triethylamine, pyridines or N-methylpiperidine, and inorganic bases, for example metal hydroxides such as sodium and potassium hydroxides or metal carbonates such as sodium carbonate or calcium carbonate.

Process variant (a) according to the invention is, where appropriate, carried out in the presence of a catalyst. Examples which may be mentioned are 4-dimethylaminopyridine, 1-hydroxy-benzotriazole or dimethylformamide.

The temperatures when carrying out process variants (a) and (b) can be varied within a relatively wide range. In general, the temperatures are at from −100° to +120° C., preferably from −60° to +50° C.

When carrying out process variant (a) according to the invention, in general 1 to 2 mol, preferably 1 to 1.5 mol of acid derivative of the formula (V) are employed per mole of the compound of the formula (I).

When carrying out process variant (b) according to the invention, equimolar amounts are preferably used. It proves advantageous in some cases to use di- or triphosgene in place of phosgene or to employ an excess of alcohol of the formula (VI).

Substituted amino acid derivatives of the general formula (IV) obtained by process variants (a) and (b) can be purified and fractionated into the components by conventional methods such as, for example, crystallization from a suitable solvent or chromatography on silica gel or aluminium oxide. Racemates can be fractionated into the individual enantiomers by customary methods.

PREPARATION EXAMPLES

Example 1

L-Valine 4-methyl-1-phenethyl-amide 5.0 g (0.035 mol) of 4-isopropyl-2,5-oxazolidinedione are added over the course of 4 to 6 hours at −10° C. to 23.6 g (0.175 mol) of 4-methyl-1-phenethyl-amine in 100 ml of acetonitrile. The reaction mixture is left to stir at room temperature for about 18 hours, and subsequently the solvent and excess amine are distilled out in vacuo. The resulting crude product can be directly employed further for preparing the compound (IV-1)

Purification under high vacuum results in 7.0 g (84.5% of theory) of L-valine 4-methyl-1-phenethyl-amide.

$^1$H—NMR (D$_6$-DMSO; δ=0.74–0.87 (dm, 6H, 2×CH$_3$), 1.33 (d, 3H, CH$_3$), 1.62 (5, 2H, NH$_2$), 1.77–1.87 (m, H, CH), 2.26 (s, 3H, CH$_3$), 2.93 (d, H, CH), 4.85–4.95 (m, H, CH) 7.09–7.21 (m, 4H, Ph), 8.13 (m, H, NH).

The following compounds of the general formula (Ia) are obtained in accordance with Example 1 and in accordance with the general process information:

TABLE 1

| Ex. No. | R$^1$ | Physical data |
|---------|-------|---------------|
| 2 | 4-Cl | m.p. 94–95° C. |
| 3 | 4-OCH$_3$ | n$_D^{20}$ = 1.4905 |

Example 2

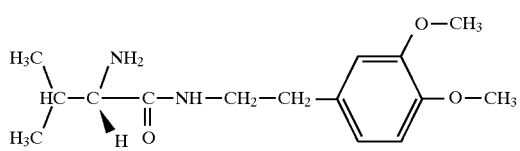

L-Valine 2-(3,4-dimethoxyphenyl)ethylamide 2.0 g (0.01398 mol) of 4-isopropyl-2,5-oxazolidinedione are added at 50° C. over the course of 2–3 hours to 10.2 g (0.055 mol) of 2-(3,4-dimethoxyphenyl)ethylamine in 60 ml of acetonitrile. The reaction mixture is left to stir for 18 hours, and subsequently the solvent and excess amine are distilled out in vacuo.

The resulting crude product is produced in adequate purity 3.5 g 90% of theory and can directly be employed further for preparing compound IV.

Characterization:
$^1$H—NMR: (D$_6$-DMSO)
δ=0.75 (d, 3H, CH$_3$), 0.84 (d, 3H, CH$_3$), 1.81–1.92 (m, H, CH), 2.65 (t, 2H, CH$_2$), 3.21–3.35 (m, 2H, CH$_2$), 3.45 (s, 2H, NH$_2$), 3.71 (s, 3H, CH$_3$), 3.74 (s, 3H, CH$_3$) 6.7–6.89 (m, 3H, aromat. protons) 7.96 (m, H, NH).

Example 3

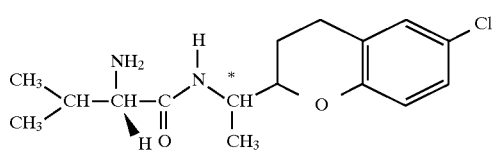

1.83 g (0.0127 mol) of 4-isopropyl-2,5-oxazolidinedione are added at 50°–55° C. over the course of 2–3 hours to 2.5 g (0.0127 mol) of 1-[2-(5-chlorobenzofuranyl)]ethylamine in 50 ml of acetonitrile. The mixture is then left to stir for 18 hours, and subsequently the solvent is distilled off. The product is purified by chromatography (silica gel CH$_2$Cl$_2$: CH$_3$OH 10:1). 1.7 g 45.5% of theory of the required product are isolated (mixture of diastereomers).

$^1$H—NMR (D$_6$-DMSO): 0.8–0.9 (dm, 6H, 2×CH$_3$), 1.48 (d, 3H, CH$_3$), 1.78–2.0 (m, H, CH), 3.02 (d, H, CH), 5.19 (m, H, CH), 2.45 (s, 2H, NH$_2$), 6.73 (m, H aromat. H), 7.24–7.68 (m, 3H aromat. H), 8.39 (m, H, NH).

PREPARATION OF THE COMPOUNDS OF THE FORMULA (IV)

Example (IV-1)

(Process variant a)

1 g (0.0043 mol) of L-valine 4-methyl-1-phenethyl-amide (compare Example 1) and 0.62 g (0.0045 mol) of potassium carbonate are suspended in 50 ml of dichloromethane at −10° C., and 0.8 g (0.0065 mol) of isopropyl chloroformate in 10 ml of methylene chloride is added. The reaction mixture is left to stir at room temperature for about 18 hours and poured into ice-water. The phases are separated, and the aqueous phase is extracted several times with methylene chloride. The combined organic phases are dried over sodium sulphate and concentrated.

1.35 g (98% of theory) of N-(isopropoxy-carbonyl)-L-valine 4-methyl-1-phenethyl-amide of melting point 160° C. are obtained.

(Process variant b)

0.1 mol of L-valine 4-methyl-1-phenethyl-amide (compare Example 1) and 0.1 mol of triethylamine are introduced into 300 ml of methylene chloride at −50° C. 0.12 mol of phosgene is passed into this solution. The reaction mixture is warmed to room temperature over the course of 4 hours. Subsequently a solution of 0.12 mol of isopropanol in 50 ml of methylene chloride is added dropwise and the mixture is stirred at 50° C. for 1 hour.

Working up results in 16.9 g of N-(isopropoxycarbonyl)-L-valine 4-methyl-1-phenethyl-amide of melting point 160° C.

We claim:
1. A compound of the formula (Ia):

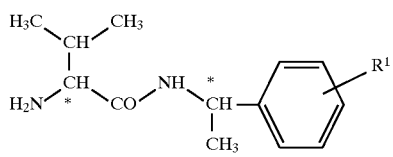 (Ia)

in which $R^1$ represents chlorine, methyl, ethyl or methoxy; or a salt thereof.

2. A pesticidal composition comprising a pesticidally effective amount of a compound or salt according to claim 1 and a carrier.

3. A method of combating unwanted pests comprising administering a pesticidally effective amount of a compound or salt according to claim 1 to the pests, their habitat or to a place from which it is desired to exclude such pests.

4. The method according to claim 3, wherein the pests are fungi and the compound or salt is applied to an above-ground part of a plant, to a seed or to the soil.

5. A process for preparing a compound according to claim 1, said process comprising reacting 4-isopropyl-2,5-oxazolidinedione of the formula:

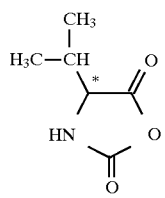

with an amine of the formula:

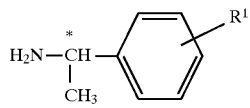

in which $R^1$ represents chlorine, methyl, ethyl or methoxy;

in the presence of a diluent and, optionally, in the presence of a reaction aid.

* * * * *

UNITED STATES PATENT AND TRADEMARK OFFICE
CERTIFICATE OF CORRECTION

PATENT NO. : 5, 814, 669
DATED : Septermber 29, 1998
INVENTOR(S) : Stelzer, et al.

It is certified that error appears in the above-identified patent and that said Letters Patent is hereby corrected as shown below:

Title Page, "PCT Pub Date"     Delete " Jan. 1 1996 " and substitute --- Jan. 11, 1996 ---

Signed and Sealed this

Eighth Day of June, 1999

Attest:

Attesting Officer

Q. TODD DICKINSON

*Acting Commissioner of Patents and Trademarks*